United States Patent [19]
Keener Jr.

[11] Patent Number: 4,732,150
[45] Date of Patent: Mar. 22, 1988

[54] PROCESS FOR CATARACT EXTRACTION

[76] Inventor: Gerald T. Keener Jr., 5455 N. Pennsylvania St., Indiana, Ind. 46220

[21] Appl. No.: 872,635

[22] Filed: Jun. 10, 1986

Related U.S. Application Data

[62] Division of Ser. No. 620,508, Jun. 14, 1984, abandoned.

[51] Int. Cl.$^4$ ............................................. A61B 17/32
[52] U.S. Cl. .................................................... 128/320
[58] Field of Search ................... 128/305, 320, 1 R; 604/22

[56] References Cited

U.S. PATENT DOCUMENTS

| | | | |
|---|---|---|---|
| 480,870 | 8/1892 | Harris | 128/320 |
| 612,569 | 10/1898 | Moscrop | 128/320 |
| 3,809,092 | 5/1974 | Abraham | 128/305 |
| 3,857,387 | 12/1974 | Shock | 128/305 X |
| 4,247,285 | 1/1981 | Roig-Greene | 128/320 X |

*Primary Examiner*—Michael H. Thaler
*Attorney, Agent, or Firm*—Woodard, Emhardt, Naughton, Moriarty & McNett

[57] ABSTRACT

A process and device for inserting a wire loop around the lens nucleus and then constricting the loop. The constricting loop divides the nucleus in half (or thirds, fourths, etc.), thus allowing it to be removed through an incision of approximately 6.5 mm.

4 Claims, 14 Drawing Figures

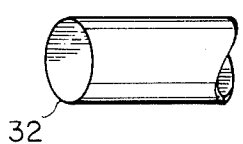
Fig.4
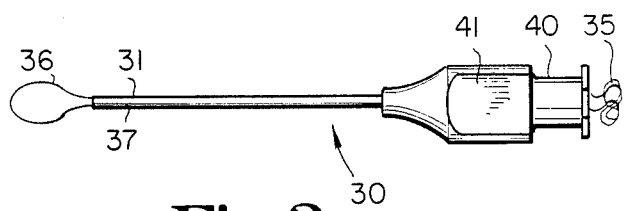
Fig.3
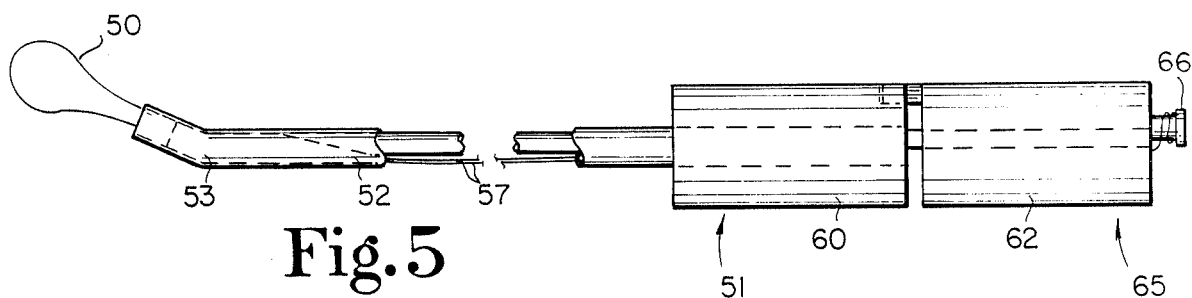
Fig.5
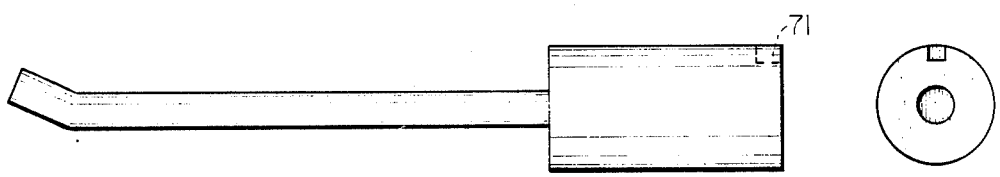
Fig.6
Fig.9
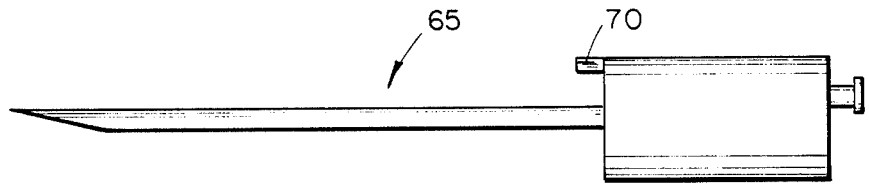
Fig.7
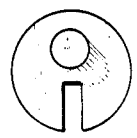
Fig.10
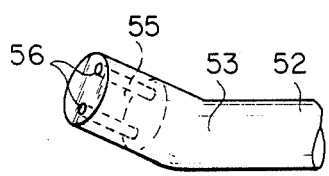
Fig.8
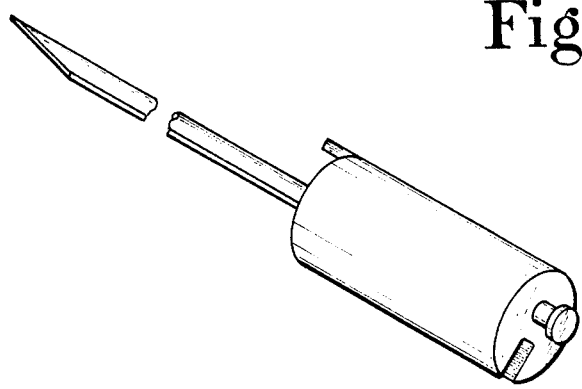
Fig.11

PROCESS FOR CATARACT EXTRACTION

This application is a division, of application Ser. No. 620,508, filed June 14, 1984, now abandoned.

BACKGROUND OF THE INVENTION

1. Field of the Invention

This invention relates to ophthalmology and more particularly to cataract extraction.

2. Description of the Prior Art

The natural lens of the eye is a lenticular-shaped body consisting of three readily distinguishable portions. The core portion is the nucleus and has the consistency of wax. Surrounding the nucleus is the cortex, a firm gelatinous material. Enclosing the cortex and constituting the wall of the lens is the capsule. "Cataract" is a medical term indicating either a degenerating or degenerated lens of the eye, or a localized point of degeneration within the lens. Cataractous degeneration results in opacification of the lens in varying degrees. As used herein, the term "cataract" is meant to imply a lens that has undergone cataractous change to an extent that the eye is visually significantly disabled.

Surgical procedures for dealing with cataracts have evolved over many centuries. Early techniques involved "couching", in which a blunt needle was inserted into the eye and used to push the lens out of the visual pathway. In the middle of the 18th century Daviel, a Frenchman, for the first time treated a cataract by removing it through an incision in the globe.

Since Daviel's time, two methods for extraction of a cataract have evolved. One is intracapsular extraction, the second, extracapsular extraction. When the cataract is removed without breaking the capsule, in other words, the lens in its entirety is removed, an intracapsular extraction is said to have been performed. By contrast, when the forward facing (anterior) portion of the capsule is removed followed by separate removal of the lens contents, an extracapsular extraction is performed. Generally, in an extracapsular extraction, the back (posterior) portion of the lens capsule is allowed to remain in the eye.

In the past 5 or 10 years, a strong trend has developed toward utilizing extracapsular technique in cataract extraction. Among other advantages felt to obtain through its use is the increased stabilization of the internal contents of the eye by virtue of retention of the posterior capsule.

In extracapsular cataract extraction, an incision is made into the eye, the anterior capsule is removed, then the nucleus is removed, following which the cortical remnants are extracted. Historically, the size of the nucleus has dictated the size of the incision which must be made for the cataract to be extracted. Since the nucleus may be as large in diameter as 10 or 10.5 mm, an incision of 10.5 to 12 mm is most commonly employed in this technique.

However, a smaller incision would present many advantages with respect to reducing operative time, increasing post-operative wound strength, hastening healing, and reducing the frequency of bleeding and infection complications. Therefore, attention has historically been given to the possibility of removing the nucleus through a smaller incision. Several years ago, a device called a phacoemulsifier was invented which allows the nucleus to be pulverized by high frequency vibrations and then aspirated. Using phacoemulsification, the lens can be removed through a 3 to 3.5 mm incision. Unfortunately, the phacoemulsifier presents potential for damaging the internal surfaces of the eye. Thus, though phacoemulsification apparatus is widely available in this country (despite its great expense), it is used in only perhaps 5% or less of cataract procedures.

SUMMARY OF THE INVENTION

One embodiment of the process of the invention might include a process for removing a cataract. The process involves peeling the conjunctival layer of the eye from the incision site at the junction of the cornea and sclera. Next, a puncture wound is made into the anterior chamber of the eye. After the puncture wound has been enlarged to provide a larger incision, the anterior capsule is removed from the cataract. Then the nucleus is displaced into the anterior chamber and the nucleus is suspended by means of a liquid in such a position that it is separated from the internal eye surfaces. The nucleus is then cut into multiple sections prior to removing the individual sections through the incision.

It is an object of the present invention to provide an improved process and instrument for performing cataract surgery. The process of the present invention involves dividing the nucleus into multiple sections so that those sections can be removed through an incision of approximately 6.5 mm or less.

BRIEF DESCRIPTION OF THE DRAWINGS

FIG. 3 is a side elevation of a nucleus dividing tool embodying the present invention.

FIG. 4 is an enlarged perspective view of the tip of the tool of FIG. 3 with the wire removed.

FIG. 5 is a side elevation of an alternative embodiment of the nucleus divider tool of FIGS. 3 and 4.

FIG. 6 is a side elevation of a component part of the tool of FIG. 5.

FIG. 7 is a side elevation of another component part of the tool of FIG. 5.

FIG. 8 is an enlarged perspective fragmentary view of the distal end of the structure of FIGS. 5 and 6.

FIG. 9 is an end elevation of the component part of FIG. 6.

FIG. 10 is an end elevation of the component part of FIG. 7.

FIG. 11 is a perspective view of the part of FIG. 7.

DETAILED DESCRIPTION OF THE PREFERRED EMBODIMENTS

Figure 1:
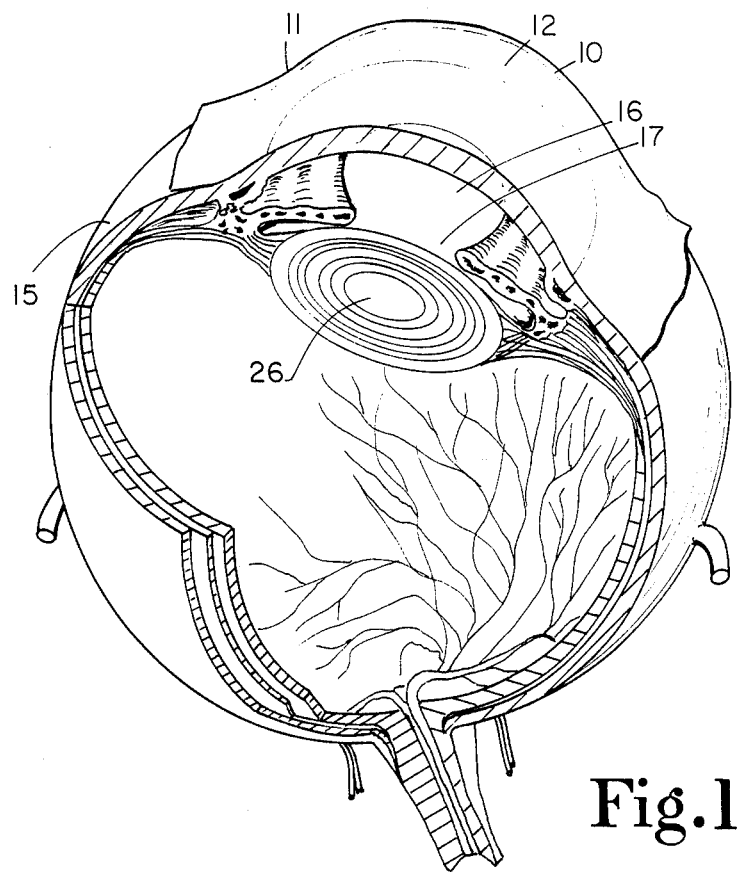
FIG. 1 is a perspective view of the eye with portions broken away to show the internal construction of the eye.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
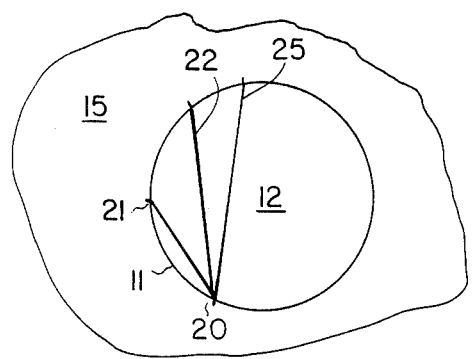
FIG. 2 is a front elevational schematic view of the eye showing an intermediate step of the process of the present invention.

Referring now more particularly to the drawings, a procedure utilizing the process and the device is illustrated. With the patient's eye paralyzed and anesthetized, (either through general or local anesthesia), the conjunctival layer 10 of the eye is peeled back from the incision site at the junction 11 of the cornea 12 and sclera 15. Referring to FIG. 2, a groove (partial thickness incision) is made along the arc or circle defined by the junction 11. The length of the groove so produced is approximately 6.5 mm. The tools used to make such an groove are well known to those skilled in the art and the procedure for making them is well known to those skilled in the art. A puncture wound into the anterior chamber 16 of the eye is made throught the groove and the anterior capsule 17 is removed from the cataract. The puncture wound is then enlarged so that an incision with a total chord length of 6.5 mm is produced. Thus, the incision will extend along the junction 11 from the point 20 to the point 21. Conventional practice normally will require the chord length of the incision to be approximately 10½ to 11½ millimeters long such as chords 22 and 25. In the present procedure, however, the chord length is relatively short and extends from the point 20 to the point 21. The incision makes possible the surgeon's access to the interior of the eye.

The nucleus of the lens 26 is next displaced into the anterior chamber. A viscous liquid, generally hyaluronic acid, (a standard substance known to those skilled in the art) is now injected into the eye so as to suspend the nucleus in a position such that it is separated from all internal eye surfaces. Such hydraulic acid is presently used by those skilled in the art in putting in implants. Such hyaluronic acid is commercially available under the trademark Healon and is marketed by Pharmacia Company of Sweden. The loop of the nucleus divider described below is then inserted around the nucleus and constricted, cutting the nucleus in half. Each half of the nucleus is separately removed through the incision, using the conventional tool called a lens loop. The cortical material remaining behind is aspirated and irrigated from the eye in conventional form. Finally the wound is sutured closed as is well known to those skilled in the art.

Variations of the incision site, size, etc., might be employed. However, an important aspect of the procedure is the employment of a device to divide the nucleus into havles or thirds or smaller sections which are small enough for evacuation through a small incision.

Referring to FIGS. 3 and 4, one embodiment of the instrument or tool embodying the present invention is illustrated. The tool consists of a cannula 30 which includes a tubular portion 31 having a blunt distal end 32. The particular cannula illustrated is manufactured by the Storz Company and marketed as a vitreous aspirating needle. The illustrated cannula is an 18 gauge thin wall and is a 25 mm straight needle and has markings at 5 mm, 10 mm and 15 mm. These markings are not needed and form no part of the present invention and are merely present because the needle or cannula is only marketed in that commercial form.

The instrument of FIGS. 3 and 4 further includes a length of 32 gauge stainless steel wire 35. This stainless steel wire is placed in the cannula in such a way that a loop 36 extends out of the distal end portion 37 of the tubular portion 31 of the instrument. The end portions of the loop of wire 36 extend through the tubular portion 31 of the cannula out the proximal end 40 of the cannula and are balled up at 35.

When the instrument of FIGS. 3 and 4 is used, the loop 36 and the distal end portion of the cannula is inserted into the incision and the nucleus is located within the loop 36. If the surgeon holds the cannula 30 at the enlarged portion 41 thereof, he can rotate the ball of wire 35 relative to the cannula, causing the loop 36 to rotate relative to the tubular portion 31 of the cannula. When it is desired to cut the nucleus into sections, the surgeon pulls on the ball of wire 35 causing the loop 36 to constrict and more partially into the tubular portion 31 of the cannula cutting the nucleus into sections. Of course, other cannulas might be used in the present invention in addition to the above described specific example of the Storz cannula.

Referring now to FIGS. 5 through 11, another embodiment of the invention is illustrated. FIG. 5 shows the nucleus divider as having a loop of wire 50 which is mounted on a base 51. The base 51 includes a tubular portion 52. FIG. 8 shows the tubular portion 52 as having a curve 53 therein in the distal end portion of the tube 52. This curve 53 facilitates manipulation of the instrument by the surgeon. In the end of the tube 52 is mounted a plug 55 which has two openings 56 therein sufficiently large in size to permit passage of the end portions 57 of the loop of wire 50. These end portions 57 extend through the enlarged portion 60 of the base 51 and through a similar enlarged portion 62 of a stylet 65 to be mounted upon a post 66 projecting from the enlarged portion 62 of the stylet 65.

FIG. 7 illustrates the stylet 65 in an unassembled condition. The stylet 65 includes a projection 70 which is received within a recess 71 whereby the enlarged portion 60 and the enlarged portion 62 are locked against rotation about the axis of the tube relative to one another. The embodiment for FIGS. 5-11 is used by locating the nucleus in the loop 50 and then by separating the enlarged portions 60 and 62. When the enlarged portions are separated, the loop 50 is constricted or caused to move into the tube 52, thus cutting the nucleus into sections.

Figure 12:
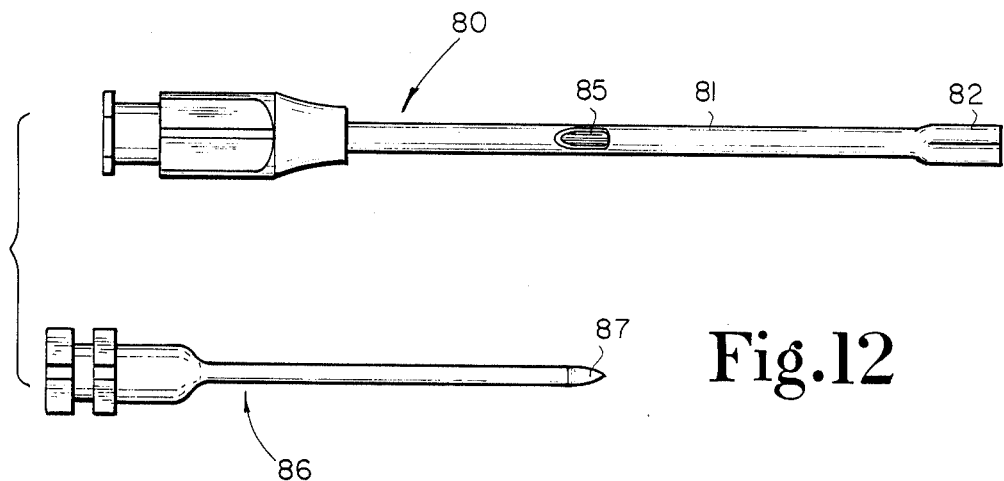
FIG. 12 is a perspective view of two components making up still another embodiment of the invention.
Figure 13:
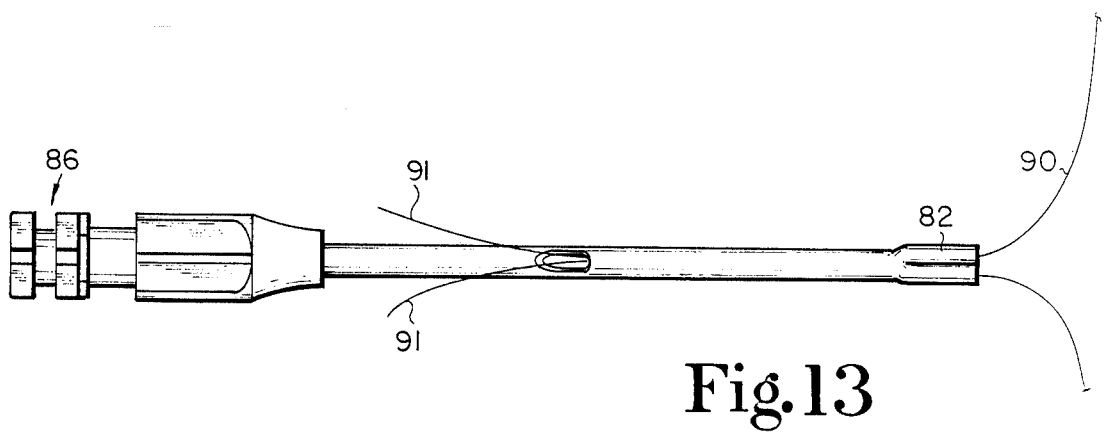
FIG. 13 shows the steps of assembling the wire on the device of FIG. 12.
Figure 14:
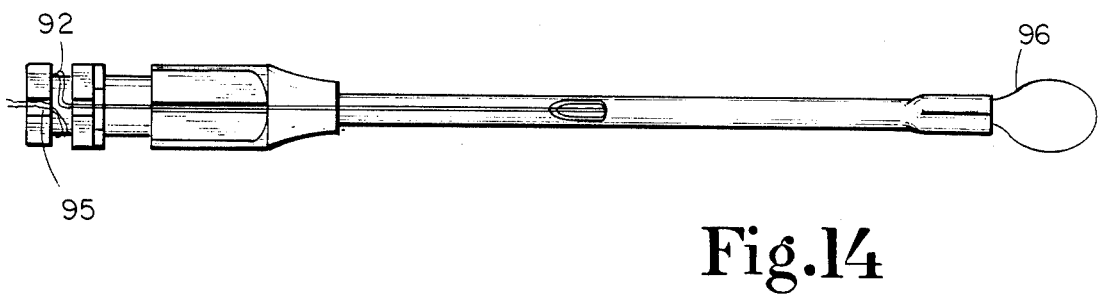
FIG. 14 shows the assembled device of FIG. 12.

Referring now to FIGS. 12, 13, and 14, still another embodiment of the nucleus divider of the present invention is illustrated. The embodiment of FIGS. 12, 13, and 14 is made from a modified Cone ventricular needle 80 NL 2112 diameter 16 gauge with one hole, working length 8.5 cm. Such a ventricular needle is marketed as a brain cannula but does not have that function in the present application. Such a product in its unmodified form is available from American V. Mueller Company. The needle 80 is modified by shortening the tubular portion 81 and by crimping the tip 82 as illustrated to form a double barrelled end on the tip 82. The cannula is further modified by cutting a notch 85 into the side of the cannula so as to allow the exit of the free ends of the 32 gauge stainless steel wire. Also shown in FIG. 12 is the stylet 86 which is shortened and has its tip tapered at 87 to provide a surface to guide the ends of the wire out of the notch 85 in the cannula.

Referring to FIG. 13, the 32 gauge stainless steel wire 90 is shown as being threaded into each of the barrels of the double barrelled tip 82, thence up the tubular portion of the cannula to the notch 85. Because the stylet 86 is telescoped within the needle 80, a tapered surface 87 is provided which causes the end portions 91 of the wire 90 to be guided out of the notch 85.

FIG. 14 shows that the free ends 91 of the wire are each formed into a loop 92 which is secured and seated into a recess 95 surrounding the stylet 86. It will be noted that the double barrelled distal end of the needle 82 permits the loop 96 to be rotated easily by merely rotating the proximal end of the instrument. Further, the loop 96 can be constricted in order to cut the nucleus into sections by partially withdrawing the stylet from the cannula whereby the wire is caused to move in the tubular portion of the cannula and to constrict the loop.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. In a process for removing a cataract including the steps of:
    (a) peeling the conjunctival layer of the eye from the incision site at the junction of the cornea and sclera;
    (b) making a puncture wound into the anterior chamber of the eye;
    (c) enlarging the puncture wound to provide a larger incision;
    (d) removing the anterior capsule from the cataract; and,
    (e) displacing the nucleus into the anterior chamber;
    the improvement which comprises the steps of:
    suspending the nucleus by means of a liquid in such a position that it is separated from internal eye surfaces; and
    cutting the nucleus in multiple sections by placing a loop of wire around the nucleus and constricting it and then removing the individual sections through the incision.

2. The process of claim 1 wherein the steps of enlarging said puncture wound is accomplished by enlarging the wound until said incision has a chord length of approximately 6.5 mm.

3. In a process for removing a cataract including the steps of:
    (a) peeling the conjunctival layer of the eye from the incision site at the junction of the cornea and sclera;
    (b) making a puncture wound into the anterior chamber of the eye;
    (c) enlarging the puncture wound to provide a larger incision;
    (d) removing the anterior capsule from the cataract; and,
    (e) displacing the nucleus into the anterior chamber;
    the improvement which comprises the steps of:
    suspending the nucleus by means of a liquid in such a position that it is separated from internal eye surfaces; and,
    dividing the nucleus in multiple sections with a wired instrument by placing a loop of wire around the nucleus and constricting it and then removing the individual sections through the incision.

4. The process of claim 3 wherein the steps of enlarging said puncture wound is accomplished by enlarging the wound until said incision has a chord length of approximately 6.5 mm.

* * * * *

UNITED STATES PATENT AND TRADEMARK OFFICE
CERTIFICATE OF CORRECTION

PATENT NO. : 4,732,150

DATED : March 22, 1988

INVENTOR(S) : Gerald T. Keener, Jr.

It is certified that error appears in the above-identified patent and that said Letters Patent is hereby corrected as shown below:

In block 76 of the title page, please change "Indiana, Ind." to --Indianapolis, Ind.--.

In column 3, line 18, please change "throught" to --through--.

In column 3, line 35, please change "hydraulic" to --hyaluronic--.

In column 3, line 51, please change "havles" to --halves--.

In column 4, line 14, please change "more" to --move--.

Signed and Sealed this

Thirteenth Day of September, 1988

Attest:

DONALD J. QUIGG

*Attesting Officer*  *Commissioner of Patents and Trademarks*